United States Patent [19]

Isshiki et al.

[11] 4,239,698

[45] Dec. 16, 1980

[54] PROCESS FOR PREPARING CARBOXYLIC ACID ANHYDRIDES

[75] Inventors: Tomiya Isshiki, Tokyo; Yasuhiko Kijima, Matsodo; Yuh Miyauchi, Mastsudo, all of Japan

[73] Assignee: Mitsubishi Gas Chemical Company, Inc., Tokyo, Japan

[21] Appl. No.: 949,853

[22] Filed: Oct. 10, 1978

[30] Foreign Application Priority Data

Oct. 11, 1977 [JP] Japan .................. 52-121772

[51] Int. Cl.³ .................. C07C 51/54; C07C 51/56
[52] U.S. Cl. .................. 260/549; 260/546
[58] Field of Search .................. 260/546, 549

[56] References Cited

U.S. PATENT DOCUMENTS

| | | | |
|---|---|---|---|
| 2,729,651 | 1/1956 | Reppe et al. | 260/549 |
| 3,927,078 | 12/1975 | Lapporte et al. | 260/549 |
| 3,989,751 | 11/1976 | Forster et al. | 260/546 |
| 4,002,678 | 1/1977 | Naglieri et al. | 260/546 |
| 4,115,444 | 9/1978 | Rizkalla | 260/549 |

FOREIGN PATENT DOCUMENTS

| | | | |
|---|---|---|---|
| 2450965 | 4/1976 | Fed. Rep. of Germany | 260/549 |
| 47-3331 | 1/1972 | Japan . | |
| 47-3332 | 1/1972 | Japan . | |
| 47-3333 | 1/1972 | Japan . | |
| 47-3334 | 1/1972 | Japan . | |
| 47-3335 | 1/1972 | Japan . | |
| 47-3336 | 1/1972 | Japan . | |
| 47-3337 | 1/1972 | Japan . | |

OTHER PUBLICATIONS

"Chemistry and Industry", 29 (5), p. 376 (1960).

*Primary Examiner*—Norman Morgenstern
*Attorney, Agent, or Firm*—Wenderoth, Lind & Ponack

[57] ABSTRACT

A process for preparing a carboxylic acid anhydride by reacting an aliphatic carboxylic acid ester or an ether with carbon monoxide in the presence of elemental nickel or a nickel compound, iodine or an iodine compound and an organic compound of a trivalent nitrogen-group element; wherein said iodine or iodine compound is selected from the following formulae (I) to (IV), $$RX_n \qquad (I)$$

wherein R represents a hydrogen atom or an alkyl or alkylene group, X represents an iodine or bromine atom, n represents an integer of 1 to 3, and at least one of n X's is an iodine atom, $$I_2 \text{ or } I_3^- \qquad (II)$$

$$RCOI \qquad (III)$$

wherein R represents an alkyl group, and $$MI_2 \qquad (IV)$$

wherein M represents an alkaline earth metal, and is used in an amount such that the free iodine or iodine compound not chemically combined with said nickel or nickel compound or with said organic compound of a nitrogen-group element is present in an amount of at least 0.2 mole, as elemental iodine, per mole of each of said nitrogen-group element compound and said nickel or nickel compound, and wherein the reaction is carried out in the presence of an aliphatic carboxylic acid solvent.

5 Claims, No Drawings

PROCESS FOR PREPARING CARBOXYLIC ACID ANHYDRIDES

This invention relates to a process for preparing carboxylic acid anhydrides by reacting carboxylic acid esters or ethers with carbon monoxide.

A process for producing carboxylic acid anhydrides by the carbonylation reaction of carboxylic acid esters or ethers is described, for example, in U.S. Pat. No. 2,729,651 (Reppe process). In this process, the reaction must be performed under severe conditions involving high temperatures and pressures, and the yield is insufficient. In an attempt to remove these defects, a method which uses a complex of a platinum-group metal typified by rhodium as a catalyst was recently developed (Japanese Patent Publications Nos. 3331/72 to 3337/72 which correspond to U.S. applications Ser. Nos. 701,637 to 701,639, 628,577, 628,578, 628,581 and 628,591). This method permits a carbonylation reaction under milder reaction conditions than in the Reppe process, and affords better yields with less amounts of by-product. Since, however, rhodium and other noble metal catalysts are very expensive, measures must be taken in commercial practice to avoid their losses by preventing the reduction of the noble metal complex to the metal in a reducing atmosphere ["Chemistry and Chemical Industry", 29 (5), p. 376 (1960)].

It is an object of this invention therefore to provide a process for preparing carboxylic acid anhydrides by the carbonylation reaction of the corresponding carboxylic acid esters or ethers under mild conditions using inexpensive catalysts without the defects associated with the prior art processes.

The above object of the invention is achieved by a process for preparing a carboxylic acid anhydride by reacting an aliphatic carboxylic acid ester or an ether with carbon monoxide in the presence of elemental nickel or a nickel compound, iodine or an iodine compound and an organic compound of a trivalent nitrogen-group element; wherein said iodine or iodine compound is selected from the following formulae (I) to (IV), $$RX_n \quad (I)$$

wherein R represents a hydrogen atom or an alkyl or alkylene group, X represents an iodine or bromine atom, n represents an integer of 1 to 3, and at least one of n X's is an iodine atom, $$I_2 \text{ or } I_3^- \quad (II)$$

$$RCOI \quad (III)$$

wherein R represents an alkyl group, and $$MI_2 \quad (IV)$$

wherein M represents an alkaline earth metal, and is used in an amount such that the free iodine or iodine compound not chemically combined with said nickel or nickel compound or with said organic compound of a nitrogen-group element is present in an amount of at least 0.2 mole, as elemental iodine, per mole of each of said nitrogen-group element compound and said nickel or nickel compound, and wherein the reaction is carried out in the presence of an aliphatic carboxylic acid solvent.

In the present invention, aliphatic carboxylic acid esters having 2 to 10 carbon atoms and aliphatic ethers having 2 to 10 carbon atoms are advantageously used as raw materials in the process of this invention. Examples of suitable carboxylates are methyl, ethyl, propyl, amyl, stearyl, and cyclohexyl esters of acetic acid, propionic acid, butyric acid, acrylic acid and crotonic acid. Examples of suitable ethers are dimethyl ether, diethyl ether, dipropyl ether, methyl ethyl ether, methyl propyl ether, ethyl propyl ether, and cyclohexyl methyl ether.

Organic or inorganic nickel compounds and elemental nickel can be used as the nickel or nickel compound (nickel component) in the process of the invention. Examples are nickel powder, nickel acetate, nickel iodide, nickel acetylacetonate, nickel carbonyl, nickel dicarbonyl, nickel dicarbonyl bistriphenyl phosphine, and nickel tetramethyl ammonium iodide.

The iodine or iodine compound selected from the formulae (I) to (IV) includes, for example, $I_2$, $KI_3$, HI, $CH_3I$, $C_2H_5I$, $C_3H_7I$, $C_4H_9I$, $CH_2I_2$, $C_2H_4I_2$, $CH_2IBr$, $CHI_3$, $C_2H_4IBr$, $CH_3COI$, $C_2H_5COI$, and $CaI_2$.

The organic compound of a trivalent nitrogen-group element (nitrogen-group component) used in this invention denotes an organic compound of trivalent nitrogen, phosphorus, arsenic or antimony.

Useful organic compounds of nitrogen include, for example, organic nitrogen compounds of the following formula (V)

(V)

wherein $R_1$, $R_2$ and $R_3$ are identical or different, and represent a hydrogen atom or an alkyl or aryl group, such as monomethylamine, dimethylamine, butylamine, trimethylamine, diethylamine, aniline and dimethyl aniline; organic nitrogen compounds of the following formula (VI)

(VI)

wherein $R_1$, $R_2$ and $R_3$ are identical or different, and represent a hydrogen atom or an alkyl or aryl group, such as dimethyl acetamide, and methyl phenyl acetamide; heterocyclic nitrogen compounds such as pyridine, hydroxyquinoline and imidazole; nitriles such as acetonitrile, propionitrile, adiponitrile and benzonitrile; and ammonium salts such as ammonium acetate.

Examples of organic compounds of phosphorus, arsenic or antimony are compounds of general formula (V) in which N is replaced by P, As or Sb, specifically trimethyl phosphine, tributyl phosphine, diphenyl phosphine, triphenyl phosphine, methyl diphenyl phosphine, triphenyl arsine, and triphenyl stibine.

Complexes of nitrogen-group compounds, such as complexes of the above-exemplified compounds with nickel or nickel carbonyl, can also be utilized in this invention.

Some of catalysts composed of these three components are known (for example, U.S. Pat. No. 2,729,651 cited hereinabove). The catalyst used in this invention is characteristic in that a free iodine component which does not react with the nickel component nor the nitrogen-group component is present in a specified amount, that is in an amount of at least 0.2 mole, preferably at least 0.5 mole, more preferably at least 1 mole, as elemental iodine per mole of each of the nitrogen-group component and the nickel component.

In some cases, the iodine or iodine compound used in this invention reacts with the other catalyst ingredients used. For example, there is a possibility that $CH_3I$ will react with $P\phi_3$ (wherein $\phi$ represents a phenyl group) to form an onium iodide compound, $(CH_3P\phi_3)I$. In this case, it is necessary to use $CH_3I$ in such an amount that the difference resulting from subtracting the amount of $CH_3I$ that reacts with $P\phi_3$ from the total amount of $CH_3I$ used is at least 0.2 mole, preferably at least 0.5 mole, more preferably at least 1 mole, as elemental iodine per mole of each of the organic nitrogen-group component and the nickel component.

In other words, the iodine or iodine compound of formula (I), (II), (III) or (IV) should be present as such in the above-specified amount.

When the organic nitrogen-group compound is a nitrile, the iodine or iodine compound is assumed to be non-reactive with the nitrogen-group compound, and the total amount of the iodine or iodine compound is regarded as the amount of the free iodine compound.

It is obvious to those skilled in the art whether or not the iodine or iodine compound reacts with a given species of the organic nitrogen-group compound used in this invention.

When the iodine compound is HI, $I_2$, $I_3^-$ or RCOI, it is assumed that the compound is reactive with the nickel or nickel compound used in this invention. Thus, the amount of the free iodine compound is the difference resulting from subtracting the amount of the iodine compound which is assumed to react with the nickel or nickel compound from the total amount of the iodine compound. Other iodine compounds are not assumed to be reactive with the nickel or nickel compound, and the total amount of such an iodine compound will be regarded as the amount of the free iodine compound.

Compounds which are formed by the reaction of the iodine or iodine compound with the other catalyst components, for example a nickel compound such as $NiI_2$ or $[(CH_3)_4N]_2NiI_4$ or an onium iodide compound such as $(CH_3P\phi_3)I$ are not included within the definition of the iodine compounds of the invention represented by formulae (I) to (IV).

If the amount of the free iodine compound is less than the above-specified amount, high yields cannot be achieved under mild reaction conditions.

When the nickel compound used in this invention is concurrently a nitrogen-group compound, for example such a compound as nickel dicarbonyl bistriphenyl phosphine or nickel tetramethyl ammonium iodide, it can be used both as a nickel component and a nitrogen-group component. Hence, so long as such a compound is used in the required amounts, another nitrogen-group compound or nickel compound need not be used. In many cases, such a compound is a coordination compound of nickel and the nitrogen-group compound.

The amount of the nickel component used in this invention is generally $10^{-6}$ to 1 mole, preferably $10^{-4}$ to $10^{-1}$ mole, per liter of the starting materials and a solvent (as will be described hereinbelow, the reaction in accordance with this invention can be performed in the presence of solvent) combined. The amount of the nitrogen-group compound required to form a stoichiometric coordination compound with nickel is $10^{-6}$ to 10 moles, preferably $10^{-4}$ to 5 moles, per liter of the starting materials and a solvent combined. As stated hereinabove, the amount of the iodine component is such that the amount of the free iodine or iodine compound is at least 0.2 mole, preferably at least 0.5 mole, more preferably at least 1 mole, as elemental iodine per mole of each of the nickel component and the nitrogen-group component. The concentration of the iodine or iodine compound per liter of the starting materials and a solvent combined is $10^{-6}$ to 20 moles, preferably $10^{-4}$ to 10 moles, as elemental iodine. When the concentration of the catalyst is high, the rate of the reaction tends to increase.

The reaction in accordance with the process of this invention may be carried out at a temperature of 50° to 300° C., preferably 100° to 250° C., and a carbon monoxide partial pressure of 0 to 1000 kg/cm$^2$.G, preferably 2 to 200 kg/cm$^2$.G, more preferably 4 to 50 kg/cm$^2$.G.

Carbon monoxide need not be of high purity, and may contain hydrogen, carbon dioxide, methane, nitrogen, rare gases, water, etc. Hydrogen does not hamper the reaction, and rather tends to stabilize the catalyst. Carbon monoxide of extremely low purity, however, is not preferred because it will increase the pressure of the reaction system.

In the present invention, it is essential to use an aliphatic carboxylic acid as a solvent. Examples of usable solvents are acetic acid, propionic acid and butyric acid. The amount of the solvent used is not particularly critical, but usually, it is used in an amount of 5 to 90% by volume, preferably 10 to 80% by volume. In the absence of the aliphatic carboxylic acid solvent, the desired product cannot be obtained in good yields.

According to the present invention, carboxylic acid anhydrides can be obtained in high yields by the carbonylation of the corresponding aliphatic carboxylic acid esters or ethers (for example, acetic anhydride from methyl acetate, or propionic anhydride from ethyl propionate or diethyl ether) under milder reaction conditions, with a carbon monoxide partial pressure of not more than 50 kg/cm$^2$.G, than in the prior art methods, and its advantages are very great.

The following examples illustrate the invention more specifically.

EXAMPLE 1

A reactor was charged with 0.58 g of nickel powder, 6.6 g of triphenyl phosphine (P$\phi_3$ for short) and 35.5 g of CH$_3$I as a catalyst, 48 g of acetic acid as a solvent, and 59.2 g of methyl acetate as a starting material. Carbon monoxide was introduced into the reactor, and the reaction was performed at a reaction temperature of 200° C. under a total pressure of 58 kg/cm$^2$.G (the partial CO pressure of 43 kg/cm$^2$.G). Five hours later, the reactor was cooled. Analysis of the reaction mixture led to the detection of 60.4 g of acetic anhydride. This shows that 74.0% of the starting material was converted to acetic anhydride. The results are shown in Table 1.

EXAMPLES 2 TO 11 AND COMPARATIVE EXAMPLE 1

The procedure of Example 1 was substantially followed using the starting materials, catalysts, solvents and reaction conditions indicted in Table 1. The results are shown in Table 1.

In Example 4, methanol was added. It changed to acetic acid under the reaction conditions and acted as a solvent.

In Example 7, the catalyst ingredient DBU is 1,8-diazabicyclo(5,4,0)-7-undecene.

In Example 11, a gaseous mixture of carbon monoxide and hydrogen was used instead of the carbon monoxide alone.

EXAMPLES 12 TO 14 AND COMPARATIVE EXAMPLE 2

The same procedure as in Example 1 was repeated using the starting materials, solvents, catalysts and reaction conditions shown in Table 2. The results are shown in Table 2.

TABLE 1

| Example | Material (amount, g) | Solvent (amount, g) | Ni compound (amount, g) | I compound (amount, g) | N-group element compound (amount, g) | Mole ratio of I/Ni | Mole ratio of I/N-group element | Temperature (°C.) | Total pressure (kg/cm². G) | CO partial pressure (kg/cm². G) | Reaction time (hours) | Yield [g, (%)] |
|---|---|---|---|---|---|---|---|---|---|---|---|---|
| 1 | Methyl acetate (59.2) | Acetic acid (48) | Ni powder (0.58) | $CH_3I$ (35.5) | $P\phi_3$ (6.6) | 22.5 | 8.9 | 200 | 58 | 43 | 5 | 60.4 (74.0) |
| 2 | Methyl acetate (59.2) | Acetic acid (48) | Ni powder (0.58) | $CaI_2$ (36.8) | $P\phi_3$ (6.6) | 22.5 | 8.9 | 200 | 56 | 43 | 6 | 59.3 (72.7) |
| 3 | Methyl acetate (59.2) | Acetic acid (48) | Nickel acetyl acetonate (2.57) | $CH_3I$ (19.3) | $P\phi_3$ (6.6) | 11.1 | 4.4 | 200 | 50 | 43 | 10 | 57.4 (70.3) |
| 4 | Methyl acetate (59.2) | Methanol (25.6) | Ni powder (0.58) | $CH_3I$ (35.5) | $P\phi_3$ (6.6) | 22.5 | 8.9 | 200 | 66 | 36 | 8 | 59.4 (72.3) |
| 5 | Methyl acetate (59.2) | Acetic acid (48) | Nickel acetyl acetonate (2.57) | $CH_3I$ (35.5) | $(n-C_4H_9)_3P$ (4.1) | 23.0 | 11.3 | 200 | 54 | 40 | 10 | 58.0 (71.1) |
| 6 | Methyl acetate (59.2) | Acetic acid (48) | Nickel acetyl acetonate (2.57) | $CH_3I$ (35.5) | $(C_2H_5)_3N$ (5.1) | 20.0 | 4.0 | 200 | 53 | 40 | 10 | 55.8 (68.4) |
| 7 | Methyl acetate (59.2) | Acetic acid (48) | Nickel acetyl acetonate (2.57) | $CH_3I$ (35.5) | DBU (6.1) | 17.0 | 2.1 | 200 | 54 | 40 | 18 | 54.9 (67.3) |
| 8 | Methyl acetate (59.2) | Acetic acid (48) | $NiI_2$ (3.12) | $CH_3I$ (35.5) | $(C_2H_5)_2NH$ (3.0) | 20.9 | 5.1 | 200 | 54 | 40 | 10 | 58.8 (72.1) |
| 9 | Methyl acetate (59.2) | Acetic acid (48) | Ni powder (1.16) | $CH_3I$ (38.6) | $P\phi_3$ (11.6) | 11.4 | 5.1 | 160 | 50 | 43 | 10 | 58.5 (71.7) |
| 10 | Diethyl ether (59.2) | Propionic acid (59.2) | Nickel acetyl acetonate (2.57) | $C_2H_5I$ (39.0) | $P\phi_3$ (6.6) | 22.5 | 8.9 | 200 | 54 | 40 | 12 | 72.9 (70.1) |
| 11 | Methyl acetate (59.2) | Acetic acid (48) | Ni powder (0.58) | $CH_3I$ (35.5) | $P\phi_3$ (6.6) | 22.5 | 8.9 | 200 | 68 | 40 ($H_2$ 10) | 4.8 | 59.9 (73.4) |
| Comp. Ex. 1 | Methyl acetate (107.3) | — | Ni powder (1.16) | $CH_3I$ (38.6) | $P\phi_3$ (11.6) | 11.4 | 5.1 | 160 | 50 | 40 | 10 | 16.1 (10.9) |

TABLE 2

| Example | Material (amount, g) | Solvent (amount, g) | Ni compound (amount, g) | I compound (amount, g) | N-group element compound (amount, g) | Mole ratio of I/Ni | Mole ratio of I/N-group element |
|---|---|---|---|---|---|---|---|
| 12 | Methyl acetate (59.2) | Acetic acid (48) | Ni powder (1) | $CH_3I$ (9) | $P\phi_3$ (12.5) | 0.91 | 0.33 |
| 13 | Ethyl acetate (70.5) | Acetic acid (48) | Ni powder (0.58) | $C_2H_5I$ (39.0) | $P\phi_3$ (6.6) | 22.5 | 8.9 |
| 14 | Methyl butyrate (172) | Butyric acid (70.5) | Ni powder (0.58) | $CH_3I$ (35.5) | $P\phi_3$ (6.6) | 22.5 | 8.9 |
| Comp. Ex. 2 | Methyl acetate (59.2) | Benzene (78) | $NiI_2$ (3) | $CH_3I$ (4) | $P\phi_3$ (6.6) | 0.31 | 0.12 |

| | Reaction conditions | | | | |
|---|---|---|---|---|---|
| | Temperature | Total pressure | CO partial pressure | Reaction time | Yield |

TABLE 2-continued

| Example | (°C.) | (kg/cm². G) | (kg/cm². G) | (hours) | [g, (%)] | |
| --- | --- | --- | --- | --- | --- | --- |
| 12 | 200 | 56 | 40 | 10 | $Ac_2O$ | 53.1 |
| | | | | | | (65.1) |
| 13 | 200 | 56 | 40 | 12 | $C_2H_5COOCOCH_3$ | 7.8 |
| | | | | | $Ac_2O$ | 23.5 |
| | | | | | $(C_2H_5CO)_2O$ | 29.8 |
| 14 | 200 | 48 | 40 | 12 | $C_3H_7COOCOCH_3$ | 13.4 |
| | | | | | $Ac_2O$ | 23.8 |
| | | | | | $(C_3H_7CO)_2O$ | 36.8 |
| Comp. Ex. 2 | 200 | 58 | 40 | 10 | $Ac_2O$ | 4.5 (5.5) |

*Ac = $CH_3CO$

What we claim is:

1. In a process for preparing a carboxylic acid anhydride by reacting an aliphatic carboxylic acid ester or an ether with carbon monoxide in the presence of a nickel component, an iodine component and a trivalent nitrogen-group element component in an aliphatic carboxylic acid solvent, the improvement which comprises using a catalyst system consisting essentially of (1) elemental nickel or a nickel compound, (2) iodine or an iodine compound and (3) an organic compound of a trivalent nitrogen-group element, wherein said iodine or iodine compound is selected from the following formulae (I) to (IV), $$RX_n \quad (I)$$

wherein R represents hydrogen, alkyl or alkylene, X represents an iodine or bromine atom, n represents an integer of 1 to 3, and at least one of n X's is an iodine atom, $$I_2 \text{ or } I_3^- \quad (II)$$

$$RCOI \quad (III)$$

wherein R represents alkyl, and $$MI_2 \quad (IV)$$

wherein M represents an alkaline earth metal, and is used in an amount such that the free iodine or iodine compound not chemically combined with said nickel or nickel compound or with said organic compound of a trivalent nitrogen-group element is present in an amount of at least 0.2 mole, as elemental iodine, per mole of each of said organic compound of a trivalent nitrogen-group element and said nickel or nickel compound.

2. The process of claim 1 wherein the organic compound of a trivalent nitrogen-group element is an organic nitrogen compound.

3. The process of claim 1 wherein the amount of the organic compound of a trivalent nitrogen-group element is $10^{-6}$ to 10 moles per liter of the starting carboxylic acid ester or ether and the solvent combined.

4. The process of claim 1 wherein the amount of the nickel or nickel compound is $10^{-6}$ to 1 mole per liter of the starting carboxylic acid ester or ether and the solvent combined.

5. The process of claim 1 wherein the free iodine or iodine compound is present in an amount of at least 0.5 mole as elemental iodine per mole of each of the organic compound of a trivalent nitrogen-group element and the nickel or nickel compound.

* * * * *